(12) United States Patent
Dickerson

(10) Patent No.: US 8,562,690 B1
(45) Date of Patent: Oct. 22, 2013

(54) MODULAR REVISION FEMORAL PROSTHESIS

(75) Inventor: Jeffrey Paul Dickerson, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 165 days.

(21) Appl. No.: 13/025,827

(22) Filed: Feb. 11, 2011

Related U.S. Application Data

(60) Provisional application No. 61/326,798, filed on Apr. 22, 2010.

(51) Int. Cl.
*A61F 2/32* (2006.01)

(52) U.S. Cl.
USPC ............ 623/22.42; 623/22.43; 623/22.44; 623/22.45; 623/22.46

(58) Field of Classification Search
USPC ............ 623/22.4, 22.41, 22.42, 23.31, 23.23, 623/23.46
See application file for complete search history.

(56) References Cited

U.S. PATENT DOCUMENTS

| | | | |
|---|---|---|---|
| 2,934,065 | A | 4/1960 | Townley |
| 4,536,894 | A | 8/1985 | Galante et al. |
| 5,002,578 | A | 3/1991 | Luman |
| 5,080,685 | A | 1/1992 | Bolesky et al. |
| 5,507,829 | A | 4/1996 | Thongpreda et al. |
| 6,863,692 | B2 | 3/2005 | Meulink |
| 7,044,975 | B2 | 5/2006 | Cheal et al. |
| 7,135,044 | B2 | 11/2006 | Bassik et al. |
| 7,175,664 | B1 | 2/2007 | Lakin |
| 7,435,263 | B2 | 10/2008 | Barnett et al. |
| 7,455,695 | B2 | 11/2008 | Khalili et al. |
| 7,575,603 | B2 | 8/2009 | Bergin et al. |
| 7,766,968 | B2 | 8/2010 | Sweeney |
| 7,776,098 | B2 | 8/2010 | Murphy |
| 7,828,805 | B2 | 11/2010 | Hoag et al. |
| 2004/0010319 | A1 | 1/2004 | McTighe et al. |
| 2005/0004679 | A1 | 1/2005 | Sederholm et al. |
| 2005/0143835 | A1 | 6/2005 | Gilbertson |
| 2005/0234559 | A1 * | 10/2005 | Fernandez et al. ......... 623/23.21 |
| 2007/0043446 | A1 | 2/2007 | Murray |
| 2007/0043448 | A1 * | 2/2007 | Murray ...................... 623/22.46 |
| 2007/0078516 | A1 | 4/2007 | Emami |
| 2007/0118229 | A1 * | 5/2007 | Bergin et al. .............. 623/23.31 |
| 2007/0173945 | A1 | 7/2007 | Wiley et al. |

(Continued)

OTHER PUBLICATIONS

Article: Femoral Revision: The Role of Modular Femoral Components, Fares Hadded et al., Ortho Supersite, accessed Apr. 20, 2010.

(Continued)

*Primary Examiner* — Bruce E Snow
*Assistant Examiner* — Brian Dukert
(74) *Attorney, Agent, or Firm* — Schwegman, Lundberg & Woessner, P.A.

(57) ABSTRACT

A femoral prosthesis for use during a revision procedure includes a proximal body, a distal stem, a modular neck, and a head. In operation, a surgeon may stabilize the proximal body and the distal stem of the prosthesis in a patient's femoral canal that has moderate loss of metaphyseal cancellous bone (known as a Paprosky Type I femoral defect), extensive loss of metaphyseal cancellous bone (known as a Paprosky Type II femoral defect), or extensive metaphyseal deterioration and some diaphyseal deterioration (known as a Paprosky Type IIIA femoral defect). Without disturbing this arrangement, the surgeon may then position the head in a desired location by selecting a desired modular neck to obtain proper joint kinematics.

17 Claims, 5 Drawing Sheets

(56) References Cited

U.S. PATENT DOCUMENTS

| | | |
|---|---|---|
| 2007/0179630 A1 | 8/2007 | Benedict et al. |
| 2008/0021567 A1* | 1/2008 | Meulink et al. ............ 623/22.12 |
| 2008/0140210 A1 | 6/2008 | Doubler et al. |
| 2008/0140211 A1 | 6/2008 | Doubler et al. |
| 2008/0281430 A1 | 11/2008 | Kelman et al. |
| 2009/0048603 A1 | 2/2009 | Hoag et al. |
| 2009/0076620 A1 | 3/2009 | Khalili et al. |
| 2009/0164026 A1 | 6/2009 | Mikami et al. |
| 2009/0270996 A1 | 10/2009 | Meulink et al. |
| 2010/0114324 A1 | 5/2010 | Gibbs et al. |
| 2011/0009973 A1 | 1/2011 | Meyers et al. |

OTHER PUBLICATIONS

Product Brochure: ZMR Hip System, Zimmer, Inc., 2004, 2008, 2009.

Zimmer Wagner SL Revision Hip Stem, Surgical Technique, Zimmer, Inc. 2007, 2009.

\* cited by examiner

MODULAR REVISION FEMORAL PROSTHESIS

CROSS REFERENCE TO RELATED APPLICATION

This application claims priority from U.S. Provisional Patent Application Ser. No. 61/326,798, entitled "MODULAR REVISION FEMORAL PROSTHESIS," filed Apr. 22, 2010, the disclosure of which is hereby expressly incorporated by reference herein in its entirety.

BACKGROUND

1. Field of the Invention

The present invention relates to a femoral prosthesis. More particularly, the present invention relates to a femoral prosthesis for use during a revision procedure, the femoral prosthesis including modular neck components.

2. Description of the Related Art

An orthopaedic prosthesis may be used to replace some or all of a patient's hip joint to restore use of the hip joint following a traumatic injury or deterioration due to aging or illness, for example. A femoral prosthesis having a stem, a neck, and a head may be used to replace a portion of the patient's femur, and a cup-shaped acetabular prosthesis may be used to replace a portion of the patient's acetabulum.

If problems develop with the original prosthesis over time, the original prosthesis may need to be removed and replaced with a new prosthesis, which is known as a revision procedure. A revision procedure may be necessary if an infection develops around the original prosthesis, if the original prosthesis experiences excessive wear or damage, or if the original prosthesis begins to loosen in the patient's bone due to deterioration of the patient's bone around the original prosthesis, for example.

Bone deterioration is a common cause of revision procedures. Designing a revision femoral prosthesis that is suitable for many patients is challenging, because the extent of bone deterioration varies greatly from patient to patient. For example, a revision patient may have moderate loss of metaphyseal cancellous bone (known as a Paprosky Type I femoral defect), extensive loss of metaphyseal cancellous bone (known as a Paprosky Type II femoral defect), or extensive metaphyseal deterioration and some diaphyseal deterioration (known as a Paprosky Type IIIA femoral defect).

SUMMARY

The present invention provides a femoral prosthesis for use during a revision procedure. The prosthesis includes a proximal body, a distal stem, a modular neck, and a head. In operation, a surgeon may stabilize the proximal body and the distal stem of the prosthesis in a patient's femoral canal that has moderate loss of metaphyseal cancellous bone (known as a Paprosky Type I femoral defect), extensive loss of metaphyseal cancellous bone (known as a Paprosky Type II femoral defect), or extensive metaphyseal deterioration and some diaphyseal deterioration (known as a Paprosky Type IIIA femoral defect). Without disturbing this arrangement, the surgeon may then position the head in a desired location by selecting a desired modular neck to obtain proper joint kinematics.

According to an embodiment of the present invention, a revision femoral prosthesis is provided for implantation in a patient's proximal femur. The prosthesis includes a proximal end, a distal end, and a longitudinal axis that extends along a length of the prosthesis from the proximal end to the distal end. The prosthesis further includes a proximal body located at the proximal end of the prosthesis, the proximal body having a cylindrical shape, a distal stem located at the distal end of the prosthesis, the distal stem tapering toward the distal end, and a modular neck removably coupled to the proximal body.

According to another embodiment of the present invention, a revision femoral prosthesis is provided for implantation in a patient's proximal femur. The prosthesis includes a proximal end, a distal end, a longitudinal axis that extends along a length of the prosthesis from the proximal end to the distal end, an anterior side, a posterior side, a medial side, and a lateral side. The prosthesis also includes a proximal body located at the proximal end of the prosthesis, a distal stem located at the distal end of the prosthesis, the distal stem tapering toward the distal end, the anterior side of the distal stem defining an anterior bevel at the distal end of the prosthesis, and the posterior side of the distal stem defining a posterior bevel at the distal end of the prosthesis, and a modular neck removably coupled to the proximal body.

According to yet another embodiment of the present invention, a method is provided for performing a revision femoral procedure after removing a previously-implanted prosthesis from the patient's femur, the patient's femur defining a space once occupied by the previously-implanted prosthesis. The method includes the steps of: selecting a prosthesis having a cylindrical proximal body and a tapered distal stem; implanting the prosthesis into the space once occupied by the previously-implanted prosthesis, the distal stem tapering distally in the patient's femur; and after the implanting step, coupling a modular neck to the proximal body of the prosthesis.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
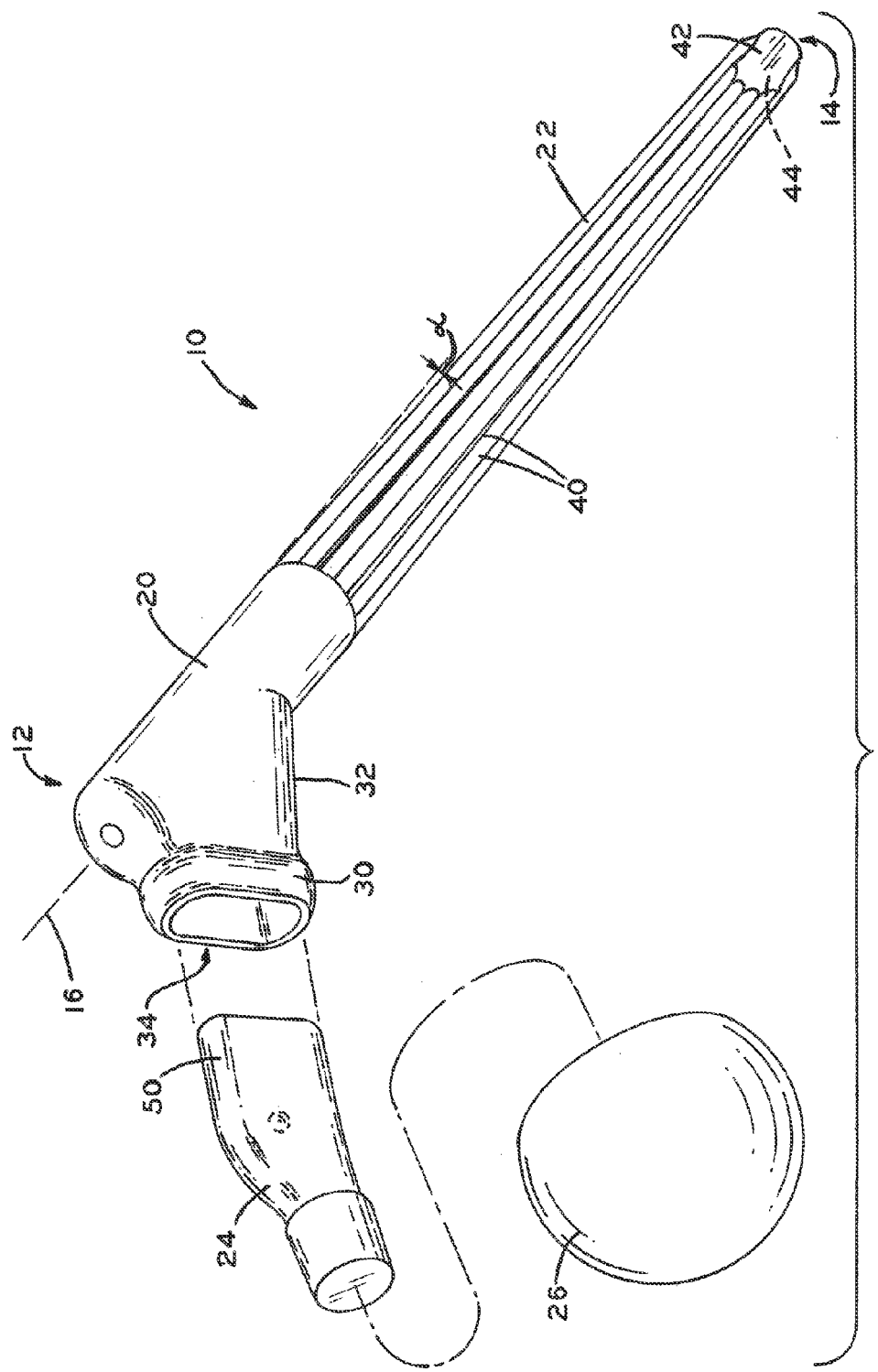
FIG. 1 is an exploded perspective view of an exemplary revision femoral prosthesis of the present invention, the prosthesis including a stem, a modular neck, and a modular head.
Figure 2:
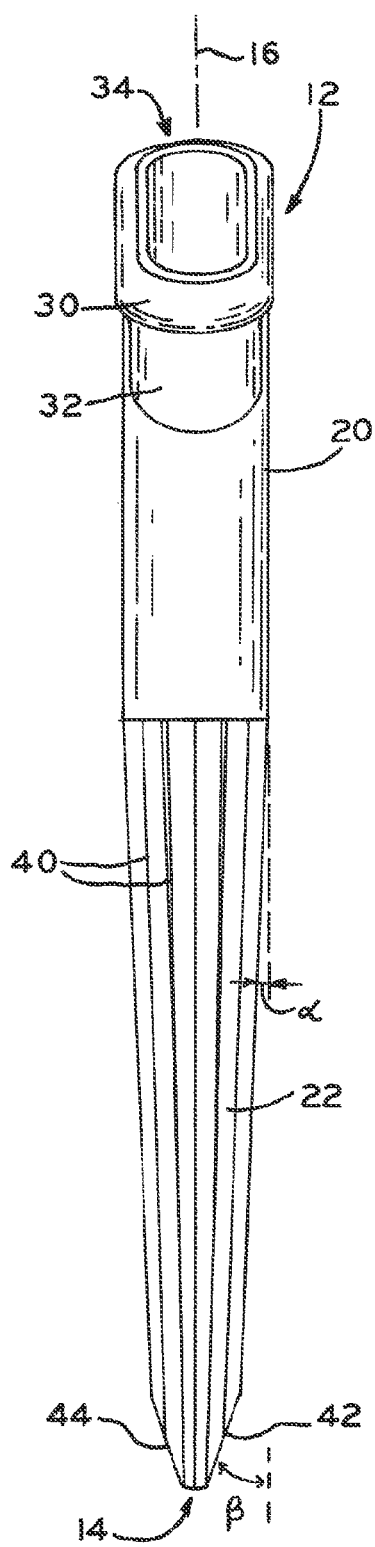
FIG. 2 is a medial elevational view of the stem of FIG. 1.
Figure 3:
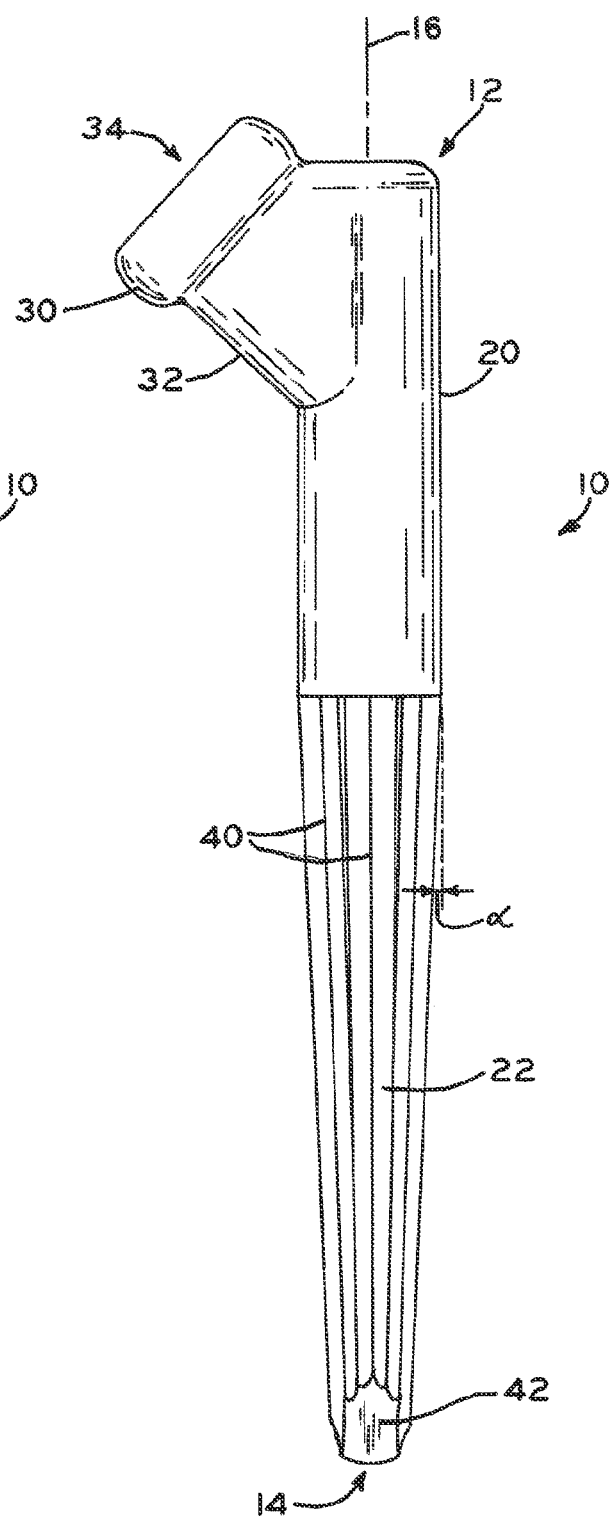
FIG. 3 is an anterior elevational view of the stem of FIG. 1.

Referring to FIGS. 1-3, an exemplary revision femoral prosthesis 10 is provided that includes proximal end 12, distal end 14, and longitudinal axis 16 that extends from proximal end 12 to distal end 14. Prosthesis 10 includes proximal body 20 located near proximal end 12, distal stem 22 located near distal end 14, a modular neck 24 that is removably coupled to proximal body 20, and a head 26 that may be integrally or removably coupled to neck 24. Prosthesis 10 may be constructed of titanium, a titanium alloy, or another suitable biocompatible material.

During a revision procedure, a previously-implanted femoral prosthesis is removed from the patient's proximal femur. The revision procedure may be necessary if, for example, the surgeon diagnoses moderate loss of metaphyseal cancellous bone (known as a Paprosky Type I femoral defect), extensive loss of metaphyseal cancellous bone (known as a Paprosky Type II femoral defect), or extensive metaphyseal deterioration and some diaphyseal deterioration (known as a Paprosky Type IIIA femoral defect). Such bone defects may cause the previously-implanted prosthesis to loosen in the patient's bone.

Following the removal step, the patient's bone may be treated or prepared, as necessary, to receive prosthesis 10 of the present invention. For example, the patient's bone may be treated with medication to reduce any infection or inflammation. Portions of the patient's bone may also be reamed if prosthesis 10 of the present invention is larger in size than the previously-implanted prosthesis.

When prosthesis 10 is implanted into the patient's proximal femur, distal stem 22 of prosthesis 10 will extend into the prepared femoral canal of the patient's femur. Neck 24 and head 26 of prosthesis 10 will project medially from the patient's femur to articulate with the patient's natural acetabulum or a prosthetic acetabular component.

According to an exemplary embodiment of the present invention, a set of prostheses may be provided in various sizes. The set may include prostheses of various lengths. For example, the set may include prostheses having lengths (measured from proximal end 12 to distal end 14) between 150 mm and 250 mm, such as lengths of 160 mm, 180 mm, 200 mm, and 220 mm. The set may also include prostheses of various diameters. For example, the diameters of proximal bodies 20 in the set may be 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, and 25 mm.

Proximal body 20 of the illustrated prosthesis 10 is cylindrical in shape, such that proximal body 20 maintains a constant circular cross-section over its length. The cylindrical geometry of proximal body 20 may minimize force transfer between proximal body 20 and the weakened metaphyseal bone of the patient's femur. As a result, the cylindrical geometry of proximal body 20 may avoid proximal stress shielding that could cause further metaphyseal bone loss from the patient's femur. Proximal body 20 may extend along as little as 20%, 25%, or 30% of the length of prosthesis 10, or along as much as 35%, 40%, or 45% of the length of prosthesis 10, or within any range delimited by any pair of the foregoing values.

At least a portion of proximal body 20 may be porous. For example, proximal body 20 may be plasma sprayed circumferentially to create an outer porous layer. When proximal body 20 is implanted into the patient's femoral canal, the porous outer layer may promote bone ingrowth. As another example, proximal body 20 may be grit blasted circumferentially to form a corundumized outer surface. When proximal body 20 is implanted into the patient's femoral canal, the corundumized outer surface may promote bone ongrowth.

It is also within the scope of the present invention that proximal body 20 may be constructed of a highly porous biomaterial. A highly porous biomaterial is useful as a bone substitute and as cell and tissue receptive material. A highly porous biomaterial may have a porosity as low as 55%, 65%, or 75% or as high as 80%, 85%, or 90%. An example of such a material is produced using Trabecular Metal™ technology generally available from Zimmer, Inc., of Warsaw, Ind. Trabecular Metal™ is a registered trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861, the disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of cancellous bone through the porous tantalum structure is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of proximal body 20 to the patient's bone.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization.

Referring still to FIGS. 1-3, proximal body 20 of prosthesis 10 includes a medial protrusion 30. In the illustrated embodiment, medial protrusion 30 has a generally rectangular cross-section, with underside 32 of medial protrusion 30 extending linearly from the cylindrical proximal body 20 to minimize contact between medial protrusion 30 and the weakened metaphyseal bone of the patient's femur. Medial protrusion 30 defines recess 34 therein that is sized to removably receive the modular neck 24. Both recess 34 and neck 24 may be tapered such that neck 24 is configured to taper couple to proximal body 20. The interaction between proximal body 20 and neck 24 is discussed further below.

It is within the scope of the present invention that proximal body 20 may include a trochanteric attachment feature, such as a threaded bore (not shown) or a plurality of suture holes (not shown). In use, prosthesis 10 may be secured to the greater trochanter of the patient's femur by inserting a screw through the greater trochanter of the patient's femur and into the threaded bore of proximal body 20 or by threading sutures into the suture holes, for example.

Distal stem 22 of the illustrated prosthesis 10 is circular in cross-section and tapers toward distal end 14 to define a taper angle α relative to longitudinal axis 16 or an axis parallel thereto. According to an exemplary embodiment of the present invention, taper angle α is approximately 3.5°. The tapered geometry of distal stem 22 may promote stability of prosthesis 10 in the patient's femur by encouraging distal stem 22 to become wedged into the patient's femoral canal. Also, the tapered geometry of distal stem 22 may evenly distribute axial and bending loads to the patient's femur to resist subsidence and stress shielding. Distal stem 22 may extend along as little as 55%, 60%, or 65% of the length of prosthesis 10, or along as much as 70%, 75%, or 80% of the length of prosthesis 10, or within any range delimited by any pair of the foregoing values, with proximal body 20 extending along the remaining length of prosthesis 10.

At least a portion of distal stem 22 may be roughened. For example, distal stem 22 may be grit blasted circumferentially to form a corundumized outer surface. When distal stem 22 is implanted into the patient's femoral canal, the corundumized outer surface may promote bone ongrowth. It is within the scope of the present disclosure that proximal body 20 may be more porous than distal stem 22, with proximal body 20 encouraging bone ingrowth to a greater extent than distal stem 22.

As shown in FIG. 1, distal stem 22 includes a plurality of longitudinal splines 40, each spline 40 projecting radially outwardly from distal stem 22. Each spline 40 may project outwardly from distal stem 22 a distance of about 0.75 mm, for example. When distal stem 22 is implanted into the patient's femoral canal, splines 40 may engage bone that surrounds the canal to provide initial fixation during insertion of prosthesis 10 and to limit rotational movement of prosthesis 10.

Distal stem 22 further includes anterior bevel 42 located at distal end 14. With anterior bevel 42 facing anteriorly during insertion of distal stem 22 into the patient's femoral canal, anterior bevel 42 may accommodate the natural anterior bow of the patient's femur while helping to prevent distal impingement and perforation of the anterior cortex. As shown in FIG. 2, anterior bevel 42 may deviate inward at a bevel angle $\beta$ relative to longitudinal axis 16 or an axis parallel thereto as low as 15°, 20°, or 25°, or as high as 30°, 35°, or 40°, or within any range delimited by any pair of the foregoing values.

According to an exemplary embodiment of the present invention, distal stem 22 further includes a posterior bevel 44 located opposite anterior bevel 42. Providing distal stem 22 with both anterior bevel 42 and posterior bevel 44 allows a single distal stem 22 to be manufactured for both right leg and left leg applications. For example, distal stem 22 of FIG. 1 may be implanted in the patient's left femur with anterior bevel 42 facing anteriorly, or the same distal stem 22 may be rotated 180° and implanted in the patient's right femur with posterior bevel 44 facing anteriorly. In this embodiment, the anterior and posterior sides of distal stem 22 (i.e., the sides having anterior bevel 42 and posterior bevel 44) differ from the medial and lateral sides of distal stem 22. As shown in FIG. 3, the medial and lateral sides of distal stem 22 continue to taper toward distal end 14 at the taper angle $\alpha$ beyond at least a portion of anterior bevel 42 and posterior bevel 44.

According to another exemplary embodiment of the present invention, proximal body 20 is integrally coupled or formed with distal stem 22. This integral arrangement may ensure a strong, stable connection between proximal body 20 and distal stem 22. Also, this integral arrangement may simplify the surgeon's preoperative planning and selection process by having to select only the total length and diameter of prosthesis 10, for example, rather than the length and diameter of proximal body 20 and distal stem 22 individually.

The instruments used to implant prosthesis 10 may include a distal reamer (not shown) and a proximal reamer (not shown). The proximal reamer may be sized to fit over the distal reamer to ensure that the reamed proximal end of the patient's femoral canal is properly aligned with the reamed distal end of the patient's femoral canal. The reamers may include etched depth markings for preparing the patient's femoral canal to receive prosthesis 10 of a desired length.

Figure 4:
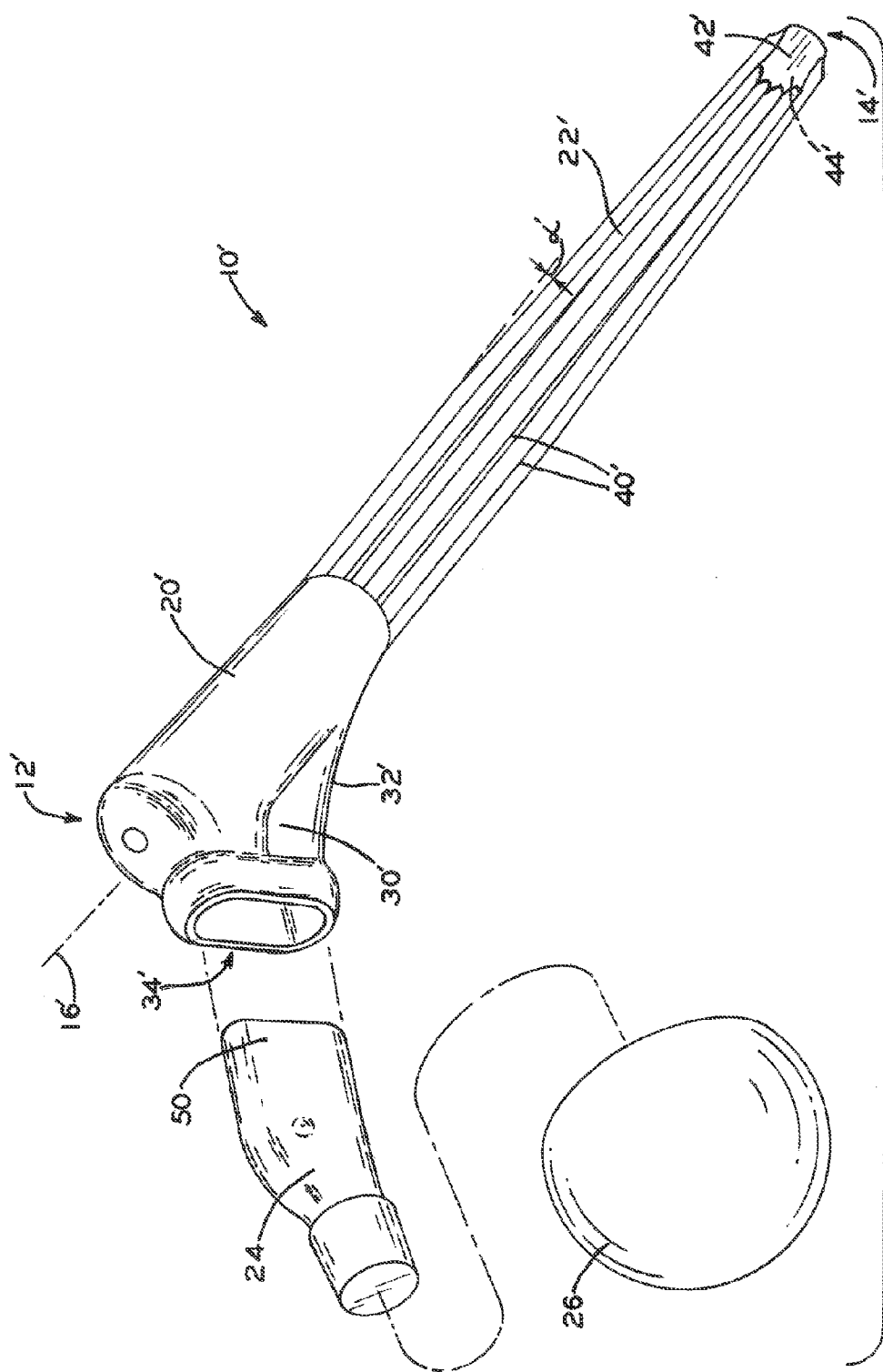
FIG. 4 is an exploded perspective view of another exemplary revision femoral prosthesis of the present invention, the prosthesis including a stem, a modular neck, and a modular head.
Figure 5:
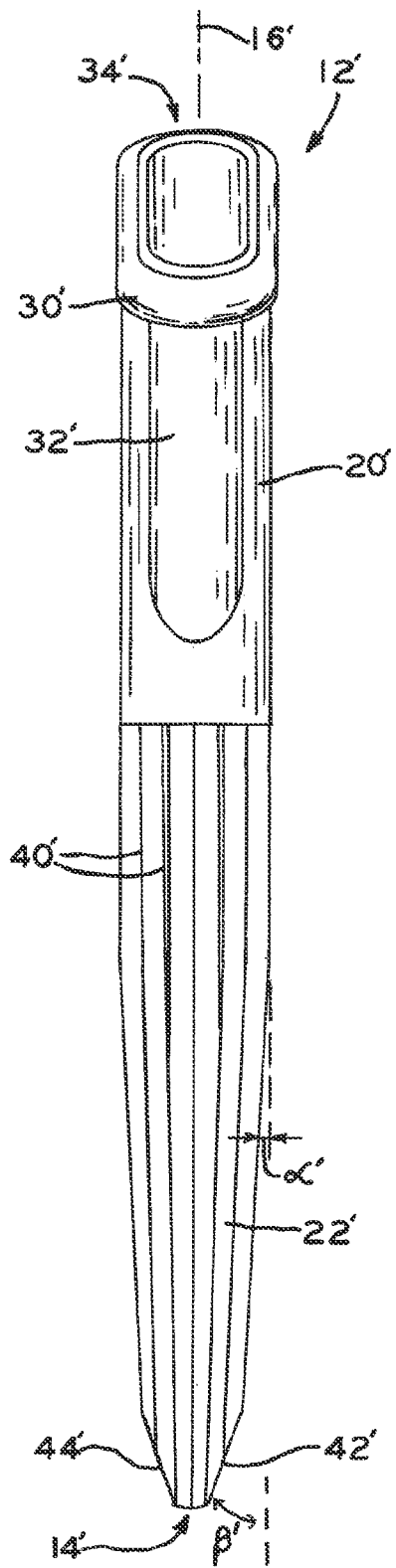
FIG. 5 is a medial elevational view of the stem of FIG. 4.
Figure 6:
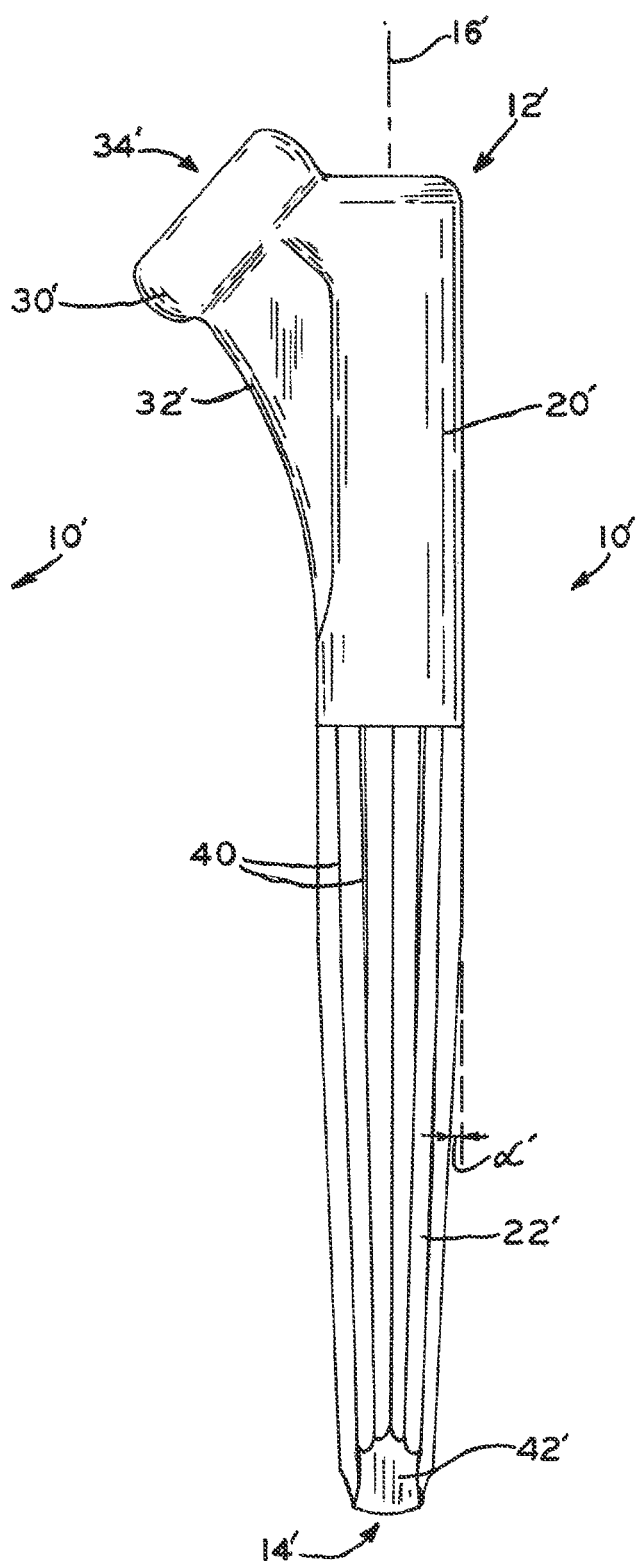
FIG. 6 is an anterior elevational view of the stem of FIG. 4.

Referring next to FIGS. 4-6, another exemplary revision femoral prosthesis 10' is illustrated. Prosthesis 10' of FIGS. 4-6 is generally similar to prosthesis 10 of FIGS. 1-3, with like reference numerals indicating like elements. Like prosthesis 10 of FIGS. 1-3, prosthesis 10' includes a medial protrusion 30' that defines recess 34' therein for receiving a modular neck 24. However, unlike medial protrusion 30 of prosthesis 10 which has a linear underside 32 (FIG. 1), medial protrusion 30' of prosthesis 10' has an arcuate underside 32' that may achieve medial fill in the patient's proximal femur.

According to an exemplary embodiment of the present invention, modular neck 24 is configured to taper couple with proximal body 20 of prosthesis 10 (FIG. 1) and/or proximal body 20' of prosthesis 10' (FIG. 4). In the illustrated embodiments, modular neck 24 includes a tapered male portion 50 that is sized and shaped for receipt within a tapered female recess 34 of proximal body 20 (FIG. 1) and/or a tapered female recess 34' of proximal body 20' (FIG. 4). However, it is also within the scope of the present invention that neck 24 may include a tapered female recess and that proximal bodies 20 and 20' may include corresponding, tapered male portions. In the illustrated embodiments, head 26 is a modular component that is removably coupled to neck 24, but as discussed above, it is also within the scope of the present invention that head 26 may be integrally coupled to neck 24.

Figure 7:
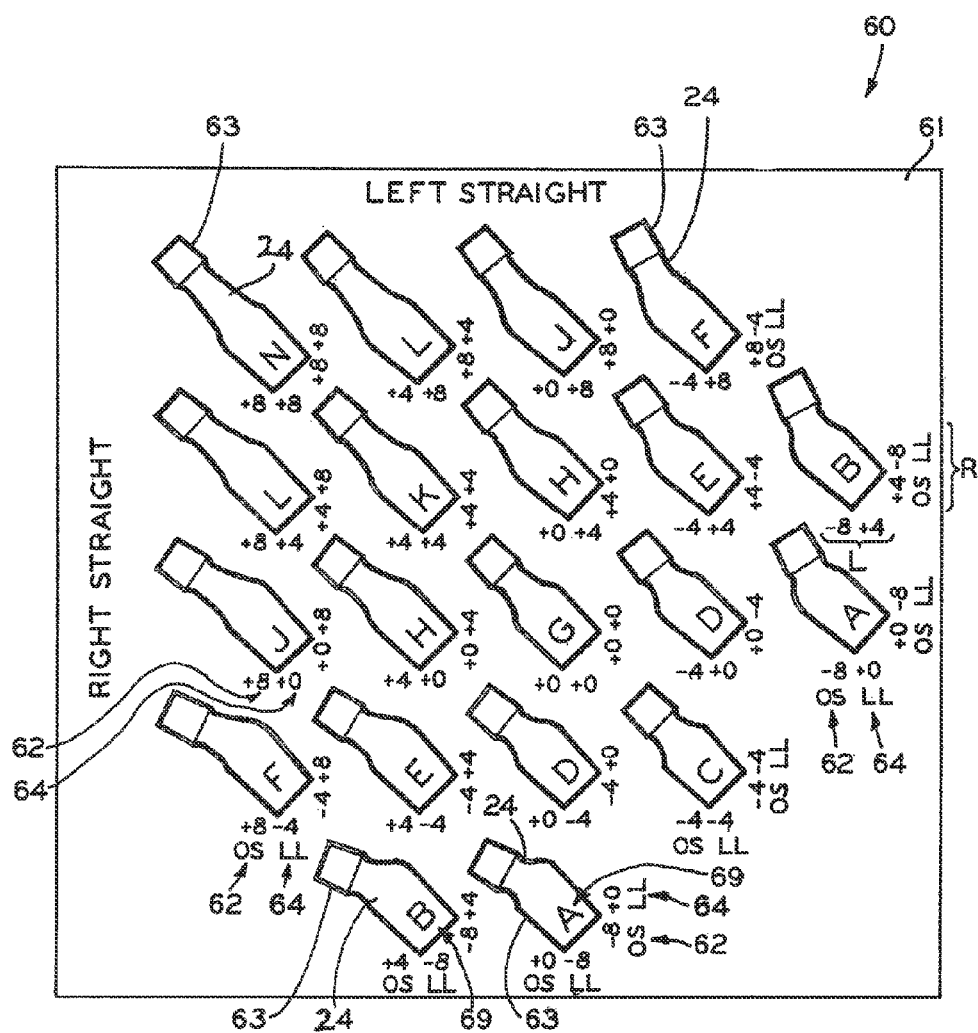
FIG. 7 is a plan view of a system of modular necks configured for use with the prostheses of FIGS. 1-6.

As shown in FIG. 7, system 60 of modular necks 24 is provided. Each neck 24 of system 60 may have an identical tapered portion 50, such that proximal body 20 of prosthesis 10 (FIG. 1) and/or proximal body 20' of prosthesis 10' (FIG. 4) are able to interchangeably receive any neck 24 from system 60. Each modular neck 24 of system 60 has a leg length dimension, an anteversion dimension, and an offset dimension that cooperate to provide a unique location for head 26. Within system 60, the leg length dimensions, the anteversion dimensions, and the offset dimensions of necks 24 vary independently.

In operation, the surgeon may determine a desired location for head 26 using a grid or a Cartesian coordinate system and may select neck 24 from system 60 that corresponds to that desired location. However, if the surgeon needs to select a different neck 24, the surgeon is able to independently vary the leg length dimension, the anteversion dimension, and/or the offset dimension without impacting the other dimensions. For example, the surgeon may select a new neck 24 having the same leg length dimension and anteversion dimension as the original neck 24, but having a different offset dimension from the original neck 24.

Advantageously, the surgeon is able to stabilize proximal body 20 and distal stem 22 of prosthesis 10 in the patient's femoral canal. The patient's femoral canal may have moderate loss of metaphyseal cancellous bone (known as a Paprosky Type I femoral defect), extensive loss of metaphyseal cancellous bone (known as a Paprosky Type II femoral defect), or extensive metaphyseal deterioration and some diaphyseal deterioration (known as a Paprosky Type IIIA femoral defect). Without disturbing this arrangement, the surgeon is then able to position head 26 in a desired location to obtain proper joint kinematics.

System 60 may include container 61 with a plurality of compartments 63 for physically housing each modular neck 24 in system 60, wherein each modular neck 24 is held in a corresponding compartment 63. Container 61 may include labels to communicate the leg length dimension, the anteversion dimension, and/or the offset dimension of each neck 24. For example, in FIG. 7, label 62 represents the offset dimension of the corresponding neck 24 and label 64 represents the leg length dimension of the corresponding neck 24. Also, each neck 24 may include reference identifier 69, such as a letter (e.g., "A", "B", etc.) or a number. In an alternative embodiment, system 60 may include a graphical representation of the plurality of modular necks 24 arranged in an organized arrangement (e.g., a Cartesian coordinate system).

Additional information regarding system 60 of modular necks 24 is set forth in U.S. patent application Ser. No. 11/458,257 to Meulink, filed Jul. 18, 2006, entitled "METHOD FOR SELECTING MODULAR IMPLANT COMPONENTS," U.S. patent application Ser. No. 11/616,369 to Meulink et al., filed Dec. 27, 2006, entitled "MODULAR ORTHOPAEDIC COMPONENT CASE," and U.S. patent application Ser. No. 12/486,791 to Meulink et al., filed Jun. 18, 2009, entitled "MODULAR ORTHOPAEDIC COMPONENTS," all assigned to the assignee of the present application, the disclosures of which are hereby expressly incorporated herein by reference.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A revision femoral prosthesis configured for implantation in a patient's proximal femur, the prosthesis including a proximal end, a distal end, and a longitudinal axis that extends along a length of the prosthesis from the proximal end to the distal end, the prosthesis comprising:
    a proximal body located at the proximal end of the prosthesis, the proximal body having a cylindrical shape, wherein a medial protrusion extends from the proximal body;
    a distal stem located at the distal end of the prosthesis, the distal stem tapering from a proximal end of the distal stem toward the distal end of the prosthesis, wherein the proximal body below the medial protrusion and above the distal stem has a constant circular cross-section along its length; and
    a modular neck removably coupled to the proximal body.

2. The prosthesis of claim 1, wherein the distal stem includes an anterior bevel located at the distal end of the prosthesis and a posterior bevel located at the distal end of the prosthesis and opposite from the anterior bevel.

3. The prosthesis of claim 1, wherein the proximal body is integrally coupled to the distal stem.

4. The prosthesis of claim 1, wherein the proximal body defines a medially-facing socket that is sized to receive the modular neck.

5. The prosthesis of claim 4, wherein the medial protrusion defines the socket, an underside of the medial protrusion being one of linear and arcuate in shape.

6. The prosthesis of claim 4, wherein the modular neck is selected from a set that includes a plurality of modular necks, each modular neck of the set being interchangeably and removably received in the socket of the proximal body.

7. The prosthesis of claim 6, further comprising at least one head, wherein the set of modular necks is configured to arrange the at least one head in a grid pattern relative to the proximal body.

8. The prosthesis of claim 6, wherein each modular neck of the set comprises a leg length dimension and an offset dimension, the leg length dimensions of the plurality of modular necks varying independently from the offset dimensions of the plurality of modular necks.

9. The prosthesis of claim 8, wherein each modular neck of the set further comprises an anteversion dimension, the anteversion dimensions of the plurality of modular necks varying independently from the leg length dimensions and the offset dimensions of the plurality of modular necks.

10. The prosthesis of claim 6, wherein the socket of the proximal body is tapered and each modular neck of the set includes a corresponding tapered protrusion that is sized to taper couple to the proximal body.

11. The prosthesis of claim 1, wherein the distal stem defines a taper angle of approximately 3.5 degrees relative to the longitudinal axis.

12. A revision femoral prosthesis configured for implantation in a patient's proximal femur, the prosthesis including a proximal end, a distal end, a longitudinal axis that extends along a length of the prosthesis from the proximal end to the distal end, an anterior side, a posterior side, a medial side, and a lateral side, the prosthesis comprising:
    a proximal body located at the proximal end of the prosthesis;
    a distal stem located at the distal end of the prosthesis, the distal stem tapering at a taper angle toward the distal end, the anterior side of the distal stem defining an anterior bevel at the distal end of the prosthesis, and the posterior side of the distal stem defining a posterior bevel at the distal end of the prosthesis, wherein a medial side and a lateral side of the distal stem taper at the taper angle beyond at least a portion of the anterior bevel and the posterior bevel; and
    a modular neck removably coupled to the proximal body.

13. The prosthesis of claim 12, wherein the proximal body includes at least one of a plasma sprayed surface and a porous tantalum structure.

14. The prosthesis of claim 12, wherein the distal stem includes a grit blasted surface.

15. The prosthesis of claim 12, wherein the proximal body extends along 25% to 40% of the length of the prosthesis and the distal stem extends along the remaining 60% to 75% of the length of the prosthesis.

16. The prosthesis of claim 12, wherein the distal stem includes a plurality of longitudinal splines, each spline projecting radially outwardly from the distal stem.

17. The prosthesis of claim 16, wherein each spline projects outwardly from the distal stem a distance of about 0.75 mm.

* * * * *